United States Patent [19]
Reiter

[11] Patent Number: 6,156,798
[45] Date of Patent: Dec. 5, 2000

[54] CYCLOBUTYL-ARYLOXYARYLSULFONYLAMINO HYDROXAMIC ACID DERIVATIVES

[75] Inventor: Lawrence A. Reiter, Mystic, Conn.

[73] Assignee: Pfizer Inc, New York, N.Y.

[21] Appl. No.: 09/290,023

[22] Filed: Apr. 9, 1999

Related U.S. Application Data

[60] Provisional application No. 60/081,392, Apr. 10, 1998.

[51] Int. Cl.[7] ........................ C07C 31/195; C07C 317/14
[52] U.S. Cl. ............................ 514/562; 560/13; 560/312; 562/427; 562/430
[58] Field of Search ..................... 560/13, 312; 562/427, 562/430; 514/562

[56] References Cited

U.S. PATENT DOCUMENTS 5,672,615   9/1997   MacPherson et al. .................. 514/357

FOREIGN PATENT DOCUMENTS

| 96/27583 | 9/1996 | WIPO . | |
| 99/07675 | 8/1997 | WIPO . | |
| 98/07697 | 2/1998 | WIPO . | |
| WO 98/07697 | 2/1998 | WIPO ......................... | C07D 211/58 |
| 98/16506 | 4/1998 | WIPO . | |

OTHER PUBLICATIONS

Database Caplus on STN, Acc. No. 1998:147308, Blumenkopf et al., 'Preparation of arylsulfonylaminohydroxamic acid derivatives as inhibitors of matrix metalloproteinase and production of tumor necrosis factor.' WO 9807697 A1 (abstract), Feb. 26, 1998.

Database Caplus of STN, Acc. No. 1999:468334, McClure et al., 'Matrix metalloprotease (MMP)–13 selective inhibitors for treatment of arthritis deformans and other MMP–related diseases.' JP 11199512 A2 (abstract), Jul. 27,1999.

Database Caplus on STN, Acc. No. 1999:464012, Doherty, 'MMP inhibitors for the treatment of ocular angiogenesis.' EP 930067 A2 (abstract), Jul. 21, 1999.

Database Caplus on STN, Acc. No. 1999:126875, Robinson, 'Preparation of aryloxyarylsulfonylaminohydroxamic acid derivatives as inhibitors of matrix metalloproteinase–13.' WO 9907675 A1 (abstract), Feb. 18, 1999.

Database Caplus on STN, Acc. No. 1998:543047, Robinson et al., 'Preparation of arylsulfonylaminoalkylhydroxamates as inhibitors fo matrix metalloproteinases or tumor necrosis factor production.' WO 9833768 A1 (abstract), Aug. 6, 1998.

*Primary Examiner*—Johann Richter
*Assistant Examiner*—Brian J. Davis
*Attorney, Agent, or Firm*—Peter C. Richardson; Paul H. Ginsburg; Seth H. Jacobs

[57] ABSTRACT

A compound of the formula

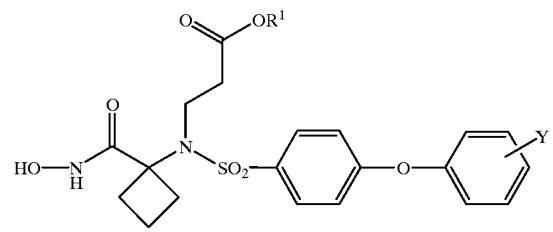

wherein Y and $R^1$ are defined in the specification, useful in the treatment of arthritis or cancer and other diseases involving selective inhibition of matrix metalloproteinase-13.

15 Claims, No Drawings

CYCLOBUTYL-ARYLOXYARYLSULFONYLAMINO HYDROXAMIC ACID DERIVATIVES

This application claims priority to provisional application Ser. No. 60/081,392 filed Apr. 10, 1998.

BACKGROUND OF THE INVENTION

The present invention relates to cyclobutyl-aryloxyarylsulfonylamino hydroxamic acid derivatives and to pharmaceutical compositions and methods of treatment.

The compounds of the present invention are inhibitors of zinc metalloendopeptidases, especially those belonging to the matrix metalloproteinase (also called MMP or matrixin) and reprolysin (also known as adamylsin) subfamilies of the metzincins (Rawlings, et al., *Methods in Enzymology*, 248, 183–228 (1995) and Stocker, et al., *Protein Science*, 4, 823–840 (1995)).

The MMP subfamily of enzymes, currently contains seventeen members (MMP-1, MMP-2, MMP-3, MMP-7, MMP-8, MMP-9, MMP-10, MMP-11, MMP-12, MMP-13, MMP-14, MMP-15, MMP-16, MMP-17, MMP-18, MMP-19, MMP-20). The MMP's are most well known for their role in regulating the turn-over of extracellular matrix proteins and as such play important roles in normal physiological processes such as reproduction, development and differentiation. In addition, the MMP's are expressed in many pathological situations in which abnormal connective tissue turnover is occurring. For example, MMP-13 an enzyme with potent activity at degrading type II collagen (the principal collagen in cartilage), has been demonstrated to be overexpressed in osteoarthritic cartilage (Mitchell, et al., *J. Clin. Invest.*, 97, 761 (1996)). Other MMPs (MMP-2, MMP-3, MMP-8, MMP-9, MMP-12) are also overexpressed in osteoarthritic cartilage and inhibition of some or all of these MMP's is expected to slow or block the accelerated loss of cartilage typical of joint diseases such as osteoarthritis or rheumatoid arthritis.

The mammalian reprolysins are known as ADAMs (A Disintegrin And Metalloproteinase) (Wolfberg, et al., *J. Cell Biol.*, 131, 275–278 (1995)) and contain a disintegrin domain in addition to a metalloproteinase-like domain. To date twenty three distinct ADAM's have been identified.

ADAM-17, also known as tumor necrosis factor-alpha converting enzyme (TACE), is the most well known ADAM. ADAM-17 (TACE) is responsible for cleavage of cell bound tumor necrosis factor-alpha (TNF-α, also known as cachectin). TNF-α is recognized to be involved in many infectious and auto-immune diseases (W. Friers, *FEBS Letters*, 285, 199 (1991)). Furthermore, it has been shown that TNF-α is the prime mediator of the inflammatory response seen in sepsis and septic shock (Spooner, et al., *Clinical Immunology and Immunopatholopy*, 62 S11 (1992)). There are two forms of TNF-α, a type II membrane protein of relative molecular mass 26,000 (26 kD) and a soluble 17 kD form generated from the cell bound protein by specific proteolytic cleavage. The soluble 17 kD form of TNF-α is released by the cell and is associated with the deleterious effects of TNF-α. This form of TNF-α is also capable of acting at sites distant from the site of synthesis. Thus, inhibitors of TACE prevent the formation of soluble TNF-α and prevent the deleterious effects of the soluble factor.

Select compounds of the invention are potent inhibitors of aggrecanase, an enzyme important in the degradation of cartilage aggrecan. Aggrecanase is also believed to be an ADAM. The loss of aggrecan from the cartilage matrix is an important factor in the progression of joint diseases such as osteoarthritis and rheumatoid arthritis and inhibition of aggrecanase is expected to slow or block the loss of cartilage in these diseases.

Other ADAMs that have shown expression in pathological situations include ADAM TS-1 (Kuno, et al., *J. Biol. Chem.*, 272, 556–562 (1997)), and ADAM's 10, 12 and 15 (Wu, et al., *Biochem. Biophvs. Res. Comm.*, 235, 437–442, (1997)). As knowledge of the expression, physiological substrates and disease association of the ADAM's increases the full significance of the role of inhibition of this class of enzymes will be appreciated.

Diseases in which inhibition of MMP's and or ADAM's will provide therapeutic benefit include: arthritis (including osteoarthritis and rheumatoid arthritis), inflammatory bowel disease, Crohn's disease, emphysema, acute respiratory distress syndrome, asthma chronic obstructive pulmonary disease, Alzheimer's disease, organ transplant toxicity, cachexia, allergic reactions, allergic contact hypersensitivity, cancer (such as solid tumor cancer including colon cancer breast cancer, lung cancer and prostrate cancer and hematopoietic malignancies including leukemias and lymphomas), tissue ulceration, restenosis, periodontal disease, epidermolysis bullosa, osteoporosis, loosening of artificial joint implants, atherosclerosis (including atherosclerotic plaque rupture), aortic aneurysm (including abdominal aortic aneurysm and brain aortic aneurysm), congestive heart failure, myocardial infarction, stroke, cerebral ischemia, head trauma, spinal cord injury, neurodegenerative disorders (acute and chronic), autoimmune disorders, Huntington's disease, Parkinson's disease, migraine, depression, peripheral neuropathy, pain, cerebral amyloid angiopathy, nootropic or cognition enhancement, amyotrophic lateral sclerosis, multiple sclerosis, ocular angiogenesis, corneal injury, macular degeneration, abnormal wound healing, burns, diabetes, tumor invasion, tumor growth, tumor metastasis, corneal scarring, scleritis, AIDS, sepsis, septic shock and other diseases characterized by metalloproteinase or ADAM expression.

This invention also relates to a method of using the compounds of the invention in the treatment of the above diseases in mammals, especially humans, and to the pharmaceutical compositions useful therefore.

It is recognized that different combinations of MMP's and ADAM's are expressed in different pathological situations. As such inhibitors with specific selectivities for individual ADAM's and/or MMP's may be preferred for individual diseases. For example, rheumatoid arthritis is an inflammatory joint disease characterized by excessive TNF levels and the loss of joint matrix constituents. In this case, a compound that inhibits TACE and aggrecanase as well as MMP's such as MMP-13 may be the preferred therapy. In contrast, in a less inflammatory joint disease such as osteoarthritis, compounds that inhibit matrix degrading MMP's such as MMP-13 but not TACE may be preferred.

The present inventors have also discovered that it is possible to design inhibitors with differential metalloprotease activity. Specifically, for example, the inventors have been able to design molecules which selectively inhibit matrix metalloprotease-13 (MMP-13) preferentially over MMP-1.

Matrix metalloproteinase inhibitors are well known in the literature. Specifically, PCT Publication WO 96/33172, published Oct. 24, 1996, refers to cyclic arylsulfonylamino hydroxamic acids that are useful as MMP inhibitors. U.S.

Pat. No. 5,672,615, PCT Publication WO 97/20824, PCT Publication WO 98/08825, PCT publication WO 98/27069, and PCT Publication WO 98/34918, published Aug. 13, 1998, entitled "Arylsulfonyl Hydroxamic Acid Derivatives" all refer to cyclic hydroxamic acids that are useful as MMP inhibitors. PCT Publications WO 96/27583 and WO 98/07697, published Mar. 7, 1996 and Feb. 26, 1998, respectively, refer to arylsulfonyl hydroxamic acids. PCT Publication WO 98/03516, published Jan. 29, 1998 refers to phosphinates with MMP activity. PCT Publication 98/34915, published Aug. 13, 1998, entitled "N-Hydroxy-b-Sulfonyl Propionamide Derivatives," refers to propionyl-hydroxamides as useful MMP inhibitors. PCT Publication WO 98/33768, published Aug. 6, 1998, entitled "Arylsulfonylamino Hydroxamic Acid Derivatives," refers to N-unsubstituted arylsulfonylamino hydroxamic acids. PCT Publication WO 98/30566, published Jul. 16, 1998, entitled "Cyclic Sulfone Derivatives," refers to cyclic sulfone hydroxamic acids as MMP inhibitors. United States Provisional Patent Application Ser. No. 60/55208, filed Aug. 8, 1997, refers to biaryl hydroxamic acids as MMP inhibitors. United States Provisional Patent Application Ser. No. 60/55207, filed Aug. 8, 1997, entitled "Aryloxyarylsulfonylamino Hydroxamic Acid Derivatives," refers to aryloxyarylsulfonyl hydroxamic acids as MMP inhibitors. United States Provisional Patent Application Ser. No. 60/62766, filed October 24, 1997, entitled "The Use of MMP-13 Selective Inhibitors For The Treatment of Osteoarthritis and Other MMP Mediated Disorders," refers to the use of MMP-13 selective inhibitors to treat inflammation and other disorders. United States Provisional Patent Application Ser. No. 60/68261, filed Dec. 19, 1997, refers to the use of MMP inhibitors to treat angiogenesis and other disorders. Each of the above referenced publications and applications is hereby incorporated by reference in its entirety.

SUMMARY OF THE INVENTION

The present invention relates to a compound of the formula

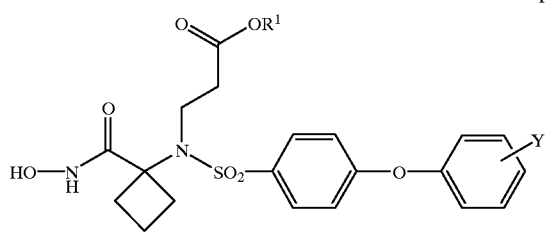

I or a pharmaceutically acceptable salt thereof, wherein $R^1$ is hydrogen or $(C_1-C_6)$alkyl; and Y is a substituent on any of the carbon atoms of the phenyl ring capable of supporting an additional bond, preferably from 1 to 2 substituents (more preferably one substituent, most preferably one substituent in the 4-position) on the phenyl ring, independently selected from hydrogen, fluoro, chloro, trifluoromethyl, $(C_1-C_6)$alkoxy, trifluoromethoxy, difluoromethoxy and $(C_1-C_6)$alkyl.

The term "alkyl", as used herein, unless otherwise indicated, includes saturated monovalent hydrocarbon radicals having straight, branched or cyclic moieties or combinations thereof.

The term "alkoxy", as used herein, includes O-alkyl groups wherein "alkyl" is defined above.

The present invention also relates to the pharmaceutically acceptable acid addition salts of compounds of the formula I. The acids which are used to prepare the pharmaceutically acceptable acid addition salts of the aforementioned base compounds of this invention are those which form non-toxic acid addition salts, i.e., salts containing pharmacologically acceptable anions, such as the hydrochloride, hydrobromide, hydroiodide, nitrate, sulfate, bisulfate, phosphate, acid phosphate, acetate, lactate, citrate, acid citrate, tartrate, bitartrate, succinate, maleate, fumarate, gluconate, saccharate, benzoate, methanesulfonate, ethanesulfonate, benzenesulfonate, p-toluenesulfonate and pamoate , [1,1'-methylene-bis-(2-hydroxy-3-naphthoate)]salts.

The invention also relates to base addition salts of formula I. The chemical bases that may be used as reagents to prepare pharmaceutically acceptable base salts of those compounds of formula I that are acidic in nature are those that form non-toxic base salts with such compounds. Such non-toxic base salts include, but are not limited to those derived from such pharmacologically acceptable cations such as alkali metal cations (eq., potassium and sodium) and alkaline earth metal cations (eq., calcium and magnesium), ammonium or water-soluble amine addition salts such as N-methylglucamine-(meglumine), and the lower alkanolammonium and other base salts of pharmaceutically acceptable organic amines.

The compound of formula I may have chiral centers and therefore exist in different enantiomeric forms. This invention relates to all optical isomers and stereoisomers of the compounds of formula I and mixtures thereof.

This invention also encompasses pharmaceutical compositions containing and methods of treating or preventing comprising administering prodrugs of compounds of the formula I. Compounds of formula I having free amino, amido, hydroxy or carboxylic groups can be converted into prodrugs. Prodrugs include compounds wherein an amino acid residue, or a polypeptide chain of two or more (e.g., two, three or four) amino acid residues which are covalently joined through peptide bonds to free amino, hydroxy or carboxylic acid groups of compounds of formula I. The amino acid residues include the 20 naturally occurring amino acids commonly designated by three letter symbols and also include, 4-hydroxyproline, hydroxylysine, demosine, isodemosine, 3-methylhistidine, norvalin, beta-alanine, gamma-aminobutyric acid, citrulline, homocysteine, homoserine, ornithine and methionine sulfone. Prodrugs also include compounds wherein carbonates, carbamates, amides and alkyl esters which are covalently bonded to the above substituents of formula I through the carbonyl carbon prodrug sidechain. Prodrugs also include compounds of formula I in which the hydroxamic acid and carbonyl moiety when taken together form a group of the formula

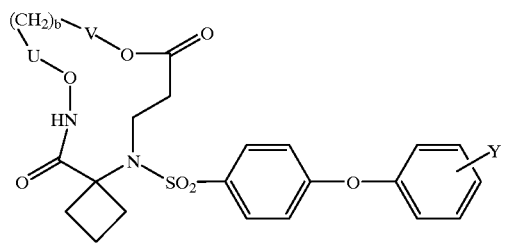

wherein Y is as defined in formula I and U and V are independently carbonyl, methylene, $SO_2$ or $SO_3$, and b is an integer from one to three wherein each methylene group is optionally substituted with hydroxy.

Preferred compounds of formula I include those wherein Y is hydrogen, fluoro or chloro, preferably 4-fluoro or 4-chloro.

Other preferred compounds of formula I include those wherein $R^1$ is hydrogen.

Specific preferred compounds of formula I include the following:

3-[[4-(4-fluorophenoxy)benzenesulfonyl]-(1-hydroxy-carbamoylcyclobutyl)amino]-propionic acid ethyl ester, and 3-[[4-(4-fluorophenoxy)benzenesulfonyl]-(1-hydroxy-carbamoylcyclobutyl) amino]propionic acid.

Other compounds of formula I include the following:

3-[(1-hydroxycarbamoylcyclobutyl)-(4-phenoxybenzenesulfonyl)amino]propionic acid, 3-[[4-(4-chlorophenoxy)benzenesulfonyl]-(1-hydroxycarbamoylcyclobutyl)amino]-propionic acid;

3-[(1-hydroxycarbamoylcyclobutyl)-(4-phenoxybenzenesulfonyl)amino]propionic acid ethyl ester; and 3-[[4-(4-chlorophenoxy)benzenesulfonyl]-(1-hydroxycarbamoylcyclobutyl)amino]-propionic acid ethyl ester.

The present invention also relates to a pharmaceutical composition for the treatment of a condition selected from the group consisting of arthritis (including osteoarthritis and rheumatoid arthritis), inflammatory bowel disease, Crohn's disease, emphysema, chronic obstructive pulmonary disease, Alzheimer's disease, organ transplant toxicity, cachexia, allergic reactions, allergic contact hypersensitivity, cancer (such as solid tumor cancer), tissue ulceration, restenosis, periodontal disease, epidermolysis bullosa, osteoporosis, loosening of artificial joint implants, atherosclerosis (including atherosclerotic plaque rupture), aortic aneurysm (including abdominal aortic aneurysm and brain aortic aneurysm), congestive heart failure, myocardial infarction, stroke, cerebral ischemia, head trauma, spinal cord injury, neuro-degenerative disorders (acute and chronic), autoimmune disorders, Huntington's disease, Parkinson's disease, migraine, depression, peripheral neuropathy, pain, cerebral amyloid angiopathy, nootropic or cognition enhancement, amyotrophic lateral sclerosis, multiple sclerosis, ocular angiogenesis, corneal injury, macular degeneration, abnormal wound healing, burns, diabetes, tumor invasion, tumor growth, tumor metastasis, corneal scarring, scleritis, AIDS, sepsis, septic shock and other diseases characterized by metalloproteinase activity and other diseases characterized by mammalian reprolysin activity in a mammal, including a human, comprising an amount of a compound of formula I or a pharmaceutically acceptable salt thereof effective in such treatments and a pharmaceutically acceptable carrier.

The present invention also relates to a pharmaceutical composition for the inhibition of (a) matrix metalloproteinases or other metalloproteinases involved in matrix degradation, or (b) a mammalian reprolysin (such as aggrecanase or ADAM's TS-1, 10, 12, 15 and 17, most preferably ADAM-17) in a mammal, including a human, comprising an effective amount of a compound of formula I or a pharmaceutically acceptable salt thereof.

The present invention also relates to a method for treating a condition selected from the group consisting of arthritis (including osteoarthritis and rheumatoid arthritis), inflammatory bowel disease, Crohn's disease, emphysema, chronic obstructive pulmonary disease, Alzheimer's disease, organ transplant toxicity, cachexia, allergic reactions, allergic contact hypersensitivity, cancer, tissue ulceration, restenosis, periodontal disease, epidermolysis bullosa, osteoporosis, loosening of artificial joint implants, atherosclerosis (including atherosclerotic plaque rupture), aortic aneurysm (including abdominal aortic aneurysm and brain aortic aneurysm), congestive heart failure, myocardial infarction, stroke, cerebral ischemia, head trauma, spinal cord injury, neuro-degenerative disorders (acute and chronic), autoimmune disorders, Huntington's disease, Parkinson's disease, migraine, depression, peripheral neuropathy, pain, cerebral amyloid angiopathy, nootropic or cognition enhancement, amyotrophic lateral sclerosis, multiple sclerosis, ocular angiogenesis, corneal injury, macular degeneration, abnormal wound healing, burns, diabetes, tumor invasion, tumor growth, tumor metastasis, corneal scarring, scleritis, AIDS, sepsis, septic shock and other diseases characterized by metalloproteinase activity and other diseases characterized by mammalian reprolysin activity in a mammal, including a human, comprising administering to said mammal an amount of a compound of formula I or a pharmaceutically acceptable salt thereof effective in treating such a condition.

The present invention also relates to a method for the inhibition of (a) matrix metalloproteinases or other metalloproteinases involved in matrix degradation, or (b) a mammalian reprolysin (such as aggrecanase or ADAM's TS-1, 10, 12, 15 and 17, preferably ADAM-17) in a mammal, including a human, comprising administering to said mammal an effective amount of a compound of formula I or a pharmaceutically acceptable salt thereof.

This invention also encompasses pharmaceutical compositions containing prodrugs of compounds of the formula I. This invention also encompasses methods of treating or preventing disorders that can be treated or prevented by the inhibition of matrix metalloproteinases or the inhibition of mammalian reprolysin comprising administering prodrugs of compounds of the formula I. Compounds of formula I having free amino, amido, hydroxy or carboxylic groups can be converted into prodrugs. Prodrugs include compounds wherein an amino acid residue, or a polypeptide chain of two or more (e.g., two, three or four) amino acid residues which are covalently joined through peptide bonds to free amino, hydroxy or carboxylic acid groups of compounds of formula I. The amino acid residues include the 20 naturally occurring amino acids commonly designated by three letter symbols and also include, 4-hydroxyproline, hydroxylysine, demosine, isodemosine, 3-methylhistidine, norvalin, beta-alanine, gamma-aminobutyric acid, citrulline, homocysteine, homoserine, omithine and methionine sulfone. Prodrugs also include compounds wherein carbonates, carbamates, amides and alkyl esters which are covalently bonded to the above substituents of formula I through the carbonyl carbon prodrug sidechain.

One of ordinary skill in the art will appreciate that the compounds of the invention are useful in treating a diverse array of diseases. One of ordinary skill in the art will also appreciate that when using the compounds of the invention in the treatment of a specific disease that the compounds of the invention may be combined with various existing therapeutic agents used for that disease.

For the treatment of rheumatoid arthritis, the compounds of the invention may be combined with agents such as TNF-α inhibitors such as anti-TNF monoclonal antibodies and TNF receptor immunoglobulin molecules (such as Enbrel®), low dose methotrexate, lefunimide, hydroxychloroquine, d-penicilamine, auranofin or parenteral or oral gold.

The compounds of the invention can also be used in combination with existing therapeutic agents for the treatment of osteoarthritis. Suitable agents to be used in combination include standard non-steroidal anti-inflammatory agents (hereinafter NSAID's) such as piroxicam, diclofenac, propionic acids such as naproxen, flubiprofen, fenoprofen, ketoprofen and ibuprofen, fenamates such as mefenamic acid, indomethacin, sulindac, apazone, pyrazolones such as phenylbutazone, salicylates such as aspirin, COX-2 inhibitors such as celecoxib and rofecoxib, analgesics and intraarticular therapies such as corticosteroids and hyaluronic acids such as hyalgan and synvisc.

The compounds of the present invention may also be used in combination with anticancer agents such as endostatin and angiostatin or cytotoxic drugs such as adriamycin, daunomycin, cis-platinum, etoposide, taxol, taxotere and alkaloids, such as vincristine, and antimetabolites such as methotrexate.

The compounds of the present invention may also be used in combination with cardiovascular agents such as calcium channel blockers, lipid lowering agents such as statins, fibrates, beta-blockers, Ace inhibitors, Angiotensin-2 receptor antagonists and platelet aggregation inhibitors.

The compounds of the present invention may also be used in combination with CNS agents such as antidepressants (such as sertraline), anti-Parkinsonian drugs (such as deprenyl, L-dopa, requip, miratex, MAOB inhibitors such as selegine and rasagiline, comP inhibitors such as Tasmar, A-2 inhibitors, dopamine reuptake inhibitors, NMDA antagonists, Nicotine agonists, Dopamine agonists and inhibitors of neuronal nitric oxide synthase), and anti-Alzheimer's drugs such as Aricept, tacrine, COX-2 inhibitors, propentofylline or metryfonate.

The compounds of the present invention may also be used in combination with osteoporosis agents such as droloxifene or fosomax and immunosuppressant agents such as FK-506 and rapamycin.

DETAILED DESCRIPTION OF THE INVENTION

The following reaction Schemes illustrate the preparation of the compounds of the present invention. Unless otherwise indicated Y and $R^1$ in the reaction Schemes and the discussion that follow are defined as above.

Scheme 1

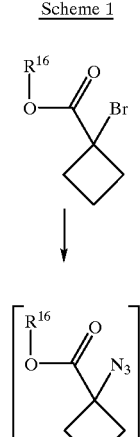

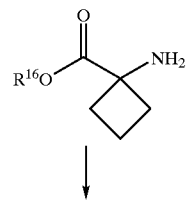

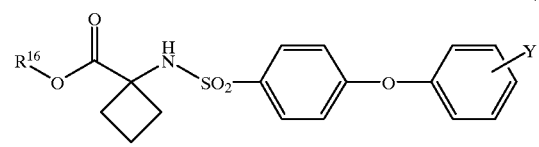

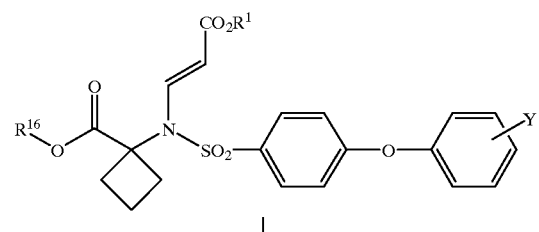

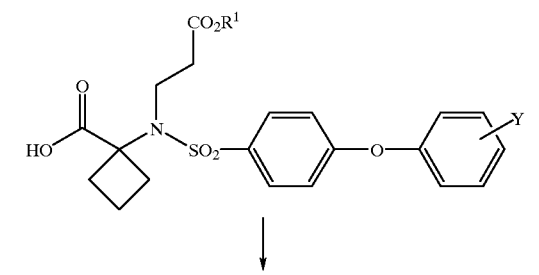

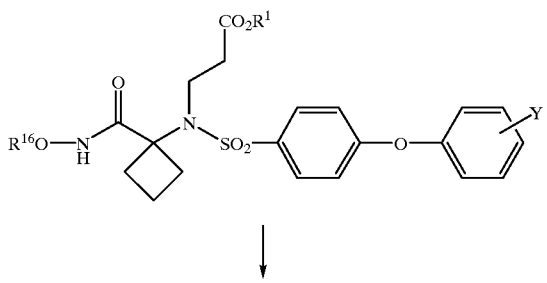

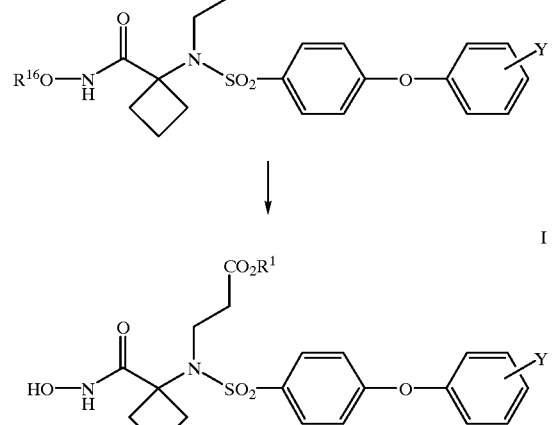

Scheme I refers to the preparation of compounds of the formula I. Referring to Scheme 1, the compound of formula I is prepared from a compound of formula II by removal of the $R^{16}$ hydroxyl amine protecting group, wherein $R^{16}$ is benzyl. Removal of the hydroxylamine protecting group is carried out by hydrogenolysis of the benzyl protecting group using catalytic palladium on barium sulfate in a polar solvent at a temperature from about 20° C. to about 25° C., i.e. room temperature, for a period of about 1 hour to about 5 hours, preferably about 3 hours.

The compound of formula II, wherein $R^{16}$ is benzyl, is prepared from a compound of formula III by activation of the compound of formula III followed by reaction with benzylhydroxylamine. The compound of formula III is activated by treatment with (benzotriazol-1-yloxy)tris (dimethylamino) phosphonium hexafluorophosphate in the presence of a base, at room temperature, in a polar solvent. The aforesaid reaction is conducted for a period of about 15 minutes to about 4 hours, preferably about 1 hour, The activated compound derived from formula III is converted in situ to the compound of formula II by reaction with benzylhydroxylamine hydrochloride. The reaction with benzylhydroxylamine hydrochloride is conducted for about 1 hour to about 5 days, preferably for about 16 hours, at a temperature of about 40° C. to about 80° C., preferably about 60° C. Suitable bases include N-methylmorpholine or diisopropylethylamine, preferably diisopropylethylamine. Suitable solvents include N,N-dimethylformamide or N-methylpyrrolidin-2-one, preferably N,N-dimethylformamide.

The compound of formula III is prepared from a compound of formula IV, wherein $R^{16}$ is benzyl, by removal of the $R^{16}$ protecting group and reduction of the side chain double bond by hydrogenolysis using palladium on carbon in a solvent such as methanol or ethanol, for a period from about 30 minutes to about 48 hours, preferably 16 hours, at a temperature of about 20° C. to about 25° C., i.e. room temperature.

The arylsulfonylamino compound of formula IV, wherein $R^{16}$ is benzyl, is prepared from the corresponding compound of formula V, by reaction with a compound of the formula $HC\equiv C-CO_2R^1$, wherein $R^1$ is ($C_1-C_6$)alkyl, in the presence of a base, such as potassium carbonate, cesium carbonate, potassium hexamethyidisilazide, sodium hydride, or tetrabutyl ammonium fluoride, preferably cesium carbonate. The reaction is stirred in a polar solvent, such as dimethylformamide, N-methylpyrrolidin-2-one or t-butanol at room temperature, for a time period between about 2 hours to about 48 hours, preferably about 18 hours.

The compound of formula V, wherein $R^{16}$ is benzyl, is prepared from the corresponding compound of formula VI by reaction with a reactive functional derivative of an arylsulfonic acid compound of the formula

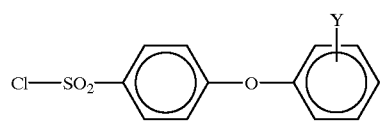

IX in the presence of a base, such as triethylamine, and a polar solvent, such as tetrahydrofuran, 1,2-dimethoxyethane, dimethylformamide, dioxane, water or acetonitrile, preferably dimethylformamide. The reaction mixture is stirred, at room temperature, for a time period between about 10 minutes to about 24 hours, preferably about 60 minutes.

Compounds of the formula VI can be prepared from compounds of formula VII by treatment with a metal azide, such as sodium azide, in a polar solvent, such as DMF, at room temperature followed by reduction of the intermediate azide of formula VII, so formed, by hydrogenolysis over palladium in an alcoholic solvent containing at least one equivalent of a mineral acid such as hydrochloric acid. The $R^{16}$ group of the formula VI can be converted to other $R^{16}$ groups by refluxing the compounds of the formula VI with an excess of the desired $R^{16}OH$ alcohol in toluene in the presence of one equivalent of p-toluene sulfonic acid.

Compounds of formula VII and IX are commercially available or can be made by methods well known to those of ordinary skill in the art.

Pharmaceutically acceptable salts of the acidic compounds of the invention are salts formed with bases, namely cationic salts such as alkali and alkaline earth metal salts, such as sodium, lithium, potassium, calcium, magnesium, as well as ammonium salts, such as ammonium, trimethylammonium, diethylammonium, and tris-(hydroxymethyl)-methylammonium slats.

Similarly acid addition salts, such as of mineral acids, organic carboxylic and organic sulfonic acids e.g. hydrochloric acid, methanesulfonic acid, maleic acid, are also possible provided a basic group, such as pyridyl, constitutes part of the structure.

The compounds of the formula I which are basic in nature are capable of forming a wide variety of different salts with various inorganic and organic acids. Although such salts must be pharmaceutically acceptable for administration to animals, it is often desirable in practice to initially isolate a compound of the formula I from the reaction mixture as a pharmaceutically unacceptable salt and then simply convert the latter back to the free base compound by treatment with an alkaline reagent, and subsequently convert the free base to a pharmaceutically acceptable acid addition salt. The acid addition salts of the base compounds of this invention are readily prepared by treating the base compound with a substantially equivalent amount of the chosen mineral or organic acid in an aqueous solvent medium or in a suitable organic solvent such as methanol or ethanol. Upon careful evaporation of the solvent, the desired solid salt is obtained.

The acids which are used to prepare the pharmaceutically acceptable acid addition salts of the base compounds of this invention are those which form non-toxic acid addition salts, i.e., salts containing pharmacologically acceptable anions, such as hydrochloride, hydrobromide, hydroiodide, nitrate, sulfate or bisulfate, phosphate or acid phosphate, acetate, lactate, citrate or acid citrate, tartrate or bitartrate, succinate, maleate, fumarate, gluconate, saccharate, benzoate, methanesulfonate and pamoate [i.e., 1,1'-methylene-bis-(2-hydroxy-3-naphthoate)] salts.

Those compounds of the formula I which are also acidic in nature, e.g., where $R^3$ is hydrogen, are capable of forming base salts with various pharmacologically acceptable cations. Examples of such salts include the alkali metal or alkaline-earth metal salts and particularly, the sodium and potassium salts. These salts are all prepared by conventional techniques. The chemical bases which are used as reagents to prepare the pharmaceutically acceptable base salts of this invention are those which form non-toxic base salts with the herein described acidic compounds of formula I. These non-toxic base salts include those derived from such pharmacologically acceptable cations as sodium, potassium, calcium and magnesium, etc. These salts can easily be prepared by treating the corresponding acidic compounds with an aqueous solution containing the desired pharmacologically acceptable cations, and then evaporating the resulting solution to dryness, preferably under reduced pressure. Alternatively, they may also be prepared by mixing lower alkanolic solutions of the acidic compounds and the desired alkali metal alkoxide together, and then evaporating the resulting solution to dryness in the same manner as before. In either case, stoichiometric quantities of reagents are preferably employed in order to ensure completeness of reaction and maximum product yields.

The ability of the compounds of formula I or their pharmaceutically acceptable salts (hereinafter also referred to as the MMP-13 selective compounds of the present invention) to inhibit matrix metalloproteinases, preferably 2, 9 or 13, most preferably MMP-13 and, consequently, demonstrate their effectiveness for treating diseases characterized by matrix metalloproteinase inhibition is shown by the following in vitro assay tests.

Biological Assay Inhibition of Human Collagenase (MMP-1)

Human recombinant collagenase is activated with trypsin using the following ratio: 10 µg trypsin per 100 µg of collagenase. The trypsin and collagenase are incubated at room temperature for 10 minutes then a five fold excess (50 µg/10 µg trypsin) of soybean trypsin inhibitor is added.

10 mM stock solutions of inhibitors are made up in dimethyl sulfoxide and then dilute using the following Scheme:

of 10 mM→120 µM→12 µM→1.2 µM→0.12 µM

Twenty-five microliters of each concentration is then added in triplicate to appropriate wells of a 96 well microfluor plate. The final concentration of inhibitor will be a 1:4 dilution after addition of enzyme and substrate. Positive controls (enzyme, no inhibitor) are set up in wells D1–D6 and blanks (no enzyme, no inhibitors) are set in wells D7–D12.

Collagenase is diluted to 400 ng/ml and 25 µl is then added to appropriate wells of the microfluor plate. Final concentration of collagenase in the assay is 100 ng/ml.

Substrate (DNP-Pro-Cha-Gly-Cys(Me)-His-Ala-Lys (NMA)-NH$_2$) is made as a 5 mM stock in dimethyl sulfoxide and then diluted to 20 mM in assay buffer. The assay is initiated by the addition of 50 µl substrate per well of the microfluor plate to give a final concentration of 10 µM.

Fluorescence readings (360 nM excitation, 460 nm emission) were taken at time 0 and then at 20 minute intervals. The assay is conducted at room temperature with a typical assay time of 3 hours.

Fluorescence vs time is then plotted for both the blank and collagenase containing samples (data from triplicate determinations is averaged). A time point that provides a good signal (the blank) and that is on a linear part of the curve (usually around 120 minutes) is chosen to determine $IC_{50}$ values. The zero time is used as a blank for each compound at each concentration and these values are subtracted from the 120 minute data. Data is plotted as inhibitor concentration vs % control (inhibitor fluorescence divided by fluorescence of collagenase alone×100). $IC_{50}$'s are determined from the concentration of inhibitor that gives a signal that is 50% of the control.

If $IC_{50}$'s are reported to be <0.03 µM then the inhibitors are assayed at concentrations of 0.3 µM, 0.03 µM, 0.03 µM and 0.003 µM.

Inhibition of MMP-13

Human recombinant MMP-13 is activated with 2 mM APMA (p-aminophenyl mercuric acetate) for 1.5 hours, at 37° C. and is diluted to 400 mg/ml in assay buffer (50 mM Tris, pH 7.5, 200 mM sodium chloride, 5 mM calcium chloride, 20 µM zinc chloride, 0.02% brij). Twenty-five microliters of diluted enzyme is added per well of a 96 well microfluor plate. The enzyme is then diluted in a 1:4 ratio in the assay by the addition of inhibitor and substrate to give a final concentration in the assay of 100 mg/ml.

10 mM stock solutions of inhibitors are made up in dimethyl sulfoxide and then diluted in assay buffer as per the inhibitor dilution scheme for inhibition of human collagenase (MMP-1): Twenty-five microliters of each concentration is added in triplicate to the microfluor plate. The final concentrations in the assay are 30 µM, 3 µM, 0.3 µM, and 0.03 µM.

Substrate (Dnp-Pro-Cha-Gly-Cys(Me)-His-Ala-Lys (NMA)-NH$_2$) is prepared as for inhibition of human collagenase (MMP-1) and 50 ml is added to each well to give a final assay concentration of 10 µM. Fluorescence readings (360 nM excitation; 450 emission) are taken at time 0 and every 5 minutes for 1 hour.

Positive controls consist of enzyme and substrate with no inhibitor and blanks consist of substrate only.

$IC_{50}$'s are determined as per inhibition of human collagenase (MMP-1). If $IC_{50}$'s are reported to be less than 0.03 µM, inhibitors are then assayed at final concentrations of 0.3 µM, 0.03 µM, 0.003 µM and 0.0003 µM.

The compounds of the present invention possess surprisingly selective activity against matrix metalloproteinase-13 (collagenase 3) as compared to matrix metalloproteinase-1 (collagenase 1). Specifically, compounds of the formula I may be 100 times more selective for matrix metalloproteinase-13 (collagenase 3) than matrix metalloproteinase-1 (collagenase 1) and have $IC_{50}$'s of less than 10 nM against matrix metalloproteinase-13 (collagenase 3). Table 1 demonstrates that the compounds of the invention possess unexpected selectivity for MMP-13 inhibition.

TABLE 1

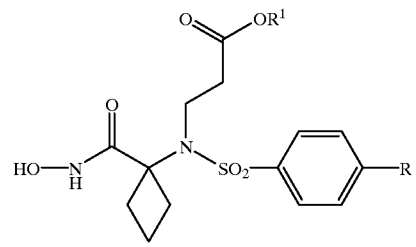

I

| Ex. | R$^1$ | R | MMP-1 IC$_{50}$ (nM) | MMP-13 IC$_{50}$ (nM) |
|---|---|---|---|---|
| 1 | H | 4-fluorophenoxy | 90 | 0.6 |
| 1 | ethyl | 4-fluorophenoxy | 18 | 0.6 |

Inhibition of Gelatinase (MMP-2)

Human recombinant 72 kD gelatinase (MMP-2, gelatinase A) is activated for 16–18 hours with 1 mM p-aminophenyl-mercuric acetate (from a freshly prepared 100 mM stock in 0.2 N NaOH) at 4° C., rocking gently.

10 mM dimethylsulfoxide stock solutions of inhibitors are diluted serially in assay buffer (50 mM TRIS, pH 7.5, 200 mM NaCl, 5 mM CaCl$_2$, 20 µM ZnCl$_2$ and 0.02% BRIJ-35 (vol./vol.)) using the following scheme:

10 mM→120 µM→12 µM→1.2 µM→0.12 µM

Further dilutions are made as necessary following this same scheme. A minimum of four inhibitor concentrations for each compound are performed in each assay. 25 µL of each concentration is then added to triplicate wells of a black 96 well U-bottomed microfluor plate. As the final assay volume is 100 AL, final concentrations of inhibitor are the result of a further 1:4 dilution (i.e. 30 µM→3 µM→0.3 µM→0.03 µM, etc.). A blank (no enzyme, no inhibitor) and a positive enzyme control (with enzyme, no inhibitor) are also prepared in triplicate.

Activated enzyme is diluted to 100 ng/mL in assay buffer, 25 µL per well is added to appropriate wells of the microplate. Final enzyme concentration in the assay is 25 ng/mL (0.34 nM).

A five mM dimethylsulfoxide stock solution of substrate (Mca-Pro-Leu-Gly-Leu-Dpa-Ala-Arg-$NH_2$) is diluted in assay buffer to 20 µM. The assay is initiated by addition of 50 µL of diluted substrate yielding a final assay concentration of 10 µM substrate. At time zero, fluorescence reading (320 excitation; 390 emission) is immediately taken and subsequent readings are taken every fifteen minutes at room temperature with a PerSeptive Biosystems CytoFluor Multi-Well Plate Reader with the gain at 90 units.

The average value of fluorescence of the enzyme and blank are plotted versus time. An early time point on the linear part of this curve is chosen for $IC_{50}$ determinations. The zero time point for each compound at each dilution is subtracted from the latter time point and the data then expressed as percent of enzyme control (inhibitor fluorescence divided by fluorescence of positive enzyme control× 100). Data is plotted as inhibitor concentration versus percent of enzyme control. $IC_{50}$'s are defined as the concentration of inhibitor that gives a signal that is 50% of the positive enzyme control.

Inhibition of Stromelysin Activity (MMP-3)

Human recombinant stromelysin (MMP-3, stromelysin-1) is activated for 20–22 hours with 2 mM p-aminophenyl-mercuric acetate (from a freshly prepared 100 mM stock in 0.2 N NaOH) at 37° C.

10 mM dimethylsulfoxide stock solutions of inhibitors are diluted serially in assay buffer (50 mM TRIS, pH 7.5, 150 mM NaCl, 10 mM $CaCl_2$ and 0.05% BRIJ-35 (vol./vol.)) using the following scheme:

10 mM→120 µM→12 µM→1.2 µM→0.12 µM

Further dilutions are made as necessary following this same scheme. A minimum of four inhibitor concentrations for each compound are performed in each assay. 25 µL of each concentration is then added to triplicate wells of a black 96 well U-bottomed microfluor plate. As the final assay volume is 100 µL, final concentrations of inhibitor are the result of a further 1:4 dilution (i.e. 30 µM→3 µM→0.3 µM→0.03 µM, etc.). A blank (no enzyme, no inhibitor) and a positive enzyme control (with enzyme, no inhibitor) are also prepared in triplicate.

Activated enzyme is diluted to 200 ng/mL in assay buffer, 25 µL per well is added to appropriate wells of the microplate. Final enzyme concentration in the assay is 50 ng/mL (0.875 nM).

A ten mM dimethylsulfoxide stock solution of substrate (Mca-Arg-Pro-Lys-Pro-Val-Glu-Nva-Trp-Arg-Lys(Dnp)-$NH_2$) is diluted in assay buffer to 6 µM. The assay is initiated by addition of 50 µL of diluted substrate yielding a final assay concentration of 3 µM substrate. At time zero, fluorescence reading (320 excitation; 390 emission) is immediately taken and subsequent readings are taken every fifteen minutes at room temperature with a PerSeptive Biosystems CytoFluor Multi-Well Plate Reader with the gain at 90 units.

The average value of fluorescence of the enzyme and blank are plotted versus time. An early time point on the linear part of this curve is chosen for $IC_{50}$ determinations. The zero time point for each compound at each dilution is subtracted from the latter time point and the data then expressed as percent of enzyme control (inhibitor fluorescence divided by fluorescence of positive enzyme control× 100). Data is plotted as inhibitor concentration versus percent of enzyme control. $IC_{50}$'s are defined as the concentration of inhibitor that gives a signal that is 50% of the positive enzyme control.

Alternatively, inhibition of stromelysin activity can be assayed using Mca-Arg-Pro-Lys-Pro-Val-Glu-Nva-Trp-Arg-Lys(Dnp)-$NH_2$ (3 µM) under conditions similar as in inhibition of human collagenase (MMP-1).

Human stromelysin is activated for 20–24 hours at 37° C. with 2 mM APMA (p-aminophenyl mercuric acetate) and is diluted to give a final concentration in the assay of 50 ng/ml. Inhibitors are diluted as for inhibition of human collagenase (MMP-1) to give final concentrations in the assay of 30 µM, 3 µM, 0.3 µM, and 0.03 µM. Each concentration is done in triplicate.

Fluorescence readings (320 nm excitation, 390 emission) are taken at time zero and then at 15 minute intervals for 3 hours.

$IC_{50}$'s are determined as per inhibition of human collagenase (MMP-1). If $IC_{50}$'s are reported to be less than 0.03 µM, then the inhibitors are assayed at final concentrations of 0.03 µM, 0.003 µM, 0.0003 µM, and 0.00003 µM.

$IC_{50}$ values were determined in the same manner as for collagenase.

Inhibition of TNF Production

The ability of the compounds or the pharmaceutically acceptable salts thereof to inhibit the production of TNF and, consequently, demonstrate their effectiveness for treating diseases involving the production of TNF is shown by the following in vitro assay:

Human mononuclear cells were isolated from anti-coagulated human blood using a one-step Ficoll-hypaque separation technique. (2) The mononuclear cells were washed three times in Hanks balanced salt solution (HBSS) with divalent cations and resuspended to a density of $2 \times 10^6$/ml in HBSS containing 1% BSA. Differential counts determined using the Abbott Cell Dyn 3500 analyzer indicated that monocytes ranged from 17 to 24% of the total cells in these preparations.

180 µl of the cell suspension was aliquoted into flat bottom 96 well plates (Costar). Additions of compounds and LPS (100 ng/ml final concentration) gave a final volume of 200 µl. All conditions were performed in triplicate. After a four hour incubation at 37° C. in an humidified $CO_2$ incubator, plates were removed and centrifuged (10 minutes at approximately 250×g) and the supernatants removed and assayed for TNFa using the R&D ELISA Kit.

Inhibition of Soluble TNF-α Production

The ability of the compounds or the pharmaceutically acceptable salts thereof to inhibit the cellular release of TNF-α and, consequently, demonstrate their effectiveness for treating diseases involving the disregulation of soluble TNF-α is shown by the following in vitro assay:

Human Monocyte Assay

Human mononuclear cells are isolated from anti-coagulated human blood using a one-step Ficoll-hypaque separation technique. (2) The mononuclear cells are washed three times in Hanks balanced salt solution (HBSS) with divalent cations and resuspended to a density of $2 \times 10^6$/ml in HBSS containing 1% BSA. Differential counts determined using the Abbott Cell Dyn 3500 analyzer indicated that monocytes ranged from 17 to 24% of the total cells in these preparations.

180 m of the cell suspension was aliquoted into flat bottom 96 well plates (Costar). Additions of compounds and LPS (100 ng/ml final concentration) gave a final volume of 200 µl. All conditions were performed in triplicate. After a four hour incubation at 37° C. in an humidified $CO_2$ incubator, plates were removed and centrifuged (10 minutes at approximately 250×g) and the supernatants removed and assayed for TNF-α using the R&D ELISA Kit.

Aggrecanase Assay

Primary porcine chondrocytes from articular joint cartilage are isolated by sequential trypsin and collagenase digestion followed by collagenase digestion overnight and are plated at 2×10$^5$ cells per well into 48 well plates with 5 μCi/ml $^{35}$S (1000 Ci/mmol) sulphur in type I collagen coated plates. Cells are allowed to incorporate label into their proteoglycan matrix (approximately 1 week) at 37° C., under an atmosphere of 5% $CO_2$.

The night before initiating the assay, chondrocyte monolayers are washed two times in DMEM/1% PSF/G and then allowed to incubate in fresh DMEM/1% FBS overnight.

The following morning chondrocytes are washed once in DMEM/1% PSF/G. The final wash is allowed to sit on the plates in the incubator while making dilutions.

Media and dilutions can be made as described in the Table below.

| | |
|---|---|
| Control Media | DMEM alone (control media) |
| IL-1 Media | DMEM + IL-1 (5 ng/ml) |
| Drug Dilutions | Make all compounds stocks at 10 mM in DMSO. Make a 100 uM stock of each compound in DMEM in 96 well plate. Store in freezer overnight. The next day perform serial dilutions in DMEM with IL-1 to 5 uM, 500 nM, and 50 nM. Aspirate final wash from wells and add 50 ul of compound from above dilutions to 450 ul of IL-1 media in appropriate wells of the 48 well plates. Final compound concentrations equal 500 nM, 50 nM, and 5 nM. All samples completed in triplicate with Control and IL-1 alone samples on each plate. |

Plates are labeled and only the interior 24 wells of the plate are used. On one of the plates, several columns are designated as IL-1 (no drug) and Control (no IL-1, no drug). These control columns are periodically counted to monitor 35S-proteoglycan release. Control and IL-1 media are added to wells (450 μl) followed by compound (50 μl) so as to initiate the assay. Plates are incubated at 37° C., with a 5% $CO_2$ atmosphere.

At 40–50 % release (when CPM from IL-1 media is 4–5 times control media) as assessed by liquid scintillation counting (LSC) of media samples, the assay is terminated (9–12 hours). Media is removed from all wells and placed in scintillation tubes. Scintillate is added and radioactive counts are acquired (LSC). To solubilize cell layers, 500 μl of papain digestion buffer (0.2 M Tris, pH 7.0, 5 mM EDTA, 5 mM DTT, and 1 mg/ml papain) is added to each well. Plates with digestion solution are incubated at 60° C. overnight. The cell layer is removed from the plates the next day and placed in scintillation tubes. Scintillate is then added, and samples counted (LSC).

The percent of released counts from the total present in each well is determined. Averages of the triplicates are made with control background subtracted from each well. The percent of compound inhibition is based on IL-1 samples as 0% inhibition (100% of total counts).

All of the compounds of the invention have $IC_{50}$ of less than 1 μM, preferably less than 5 nM. One group of most preferred compounds of the invention is at least 100 fold less potent against r-MMP-1 than in the above TACE assay. Another group of most preferred compounds is at least 100 fold less potent against MMP-1 than against MMP13. Another group of most preferred compounds is at least 100 fold less potent against MMP-1 than against aggrecanase.

For administration to humans for the inhibition of matrix metalloproteinase-13 or the production of tumor necrosis factor (TNF), a variety of conventional routes may be used including orally, parenterally and topically. In general, the active compound will be administered orally or parenterally at dosages between about 0.1 and 25 mg/kg body weight of the subject to be treated per day, preferably from about 0.3 to 5 mg/kg. However, some variation in dosage will necessarily occur depending on the condition of the subject being treated. The person responsible for administration will, in any event, determine the appropriate dose for the individual subject.

The compounds of the present invention can be administered in a wide variety of different dosage forms, in general, the therapeutically effective compounds of this invention are present in such dosage forms at concentration levels ranging from about 5.0% to about 70% by weight.

For oral administration, tablets containing various excipients such as microcrystalline cellulose, sodium citrate, calcium carbonate, dicalcium phosphate and glycine may be employed along with various disintegrants such as starch (and preferably corn, potato or tapioca starch), alginic acid and certain complex silicates, together with granulation binders like polyvinylpyrrolidone, sucrose, gelation and acacia. Additionally, lubricating agents such as magnesium stearate, sodium lauryl sulfate and talc are often very useful for tabletting purposes. Solid compositions of a similar type may also be employed as fillers in gelatin capsules; preferred materials in this connection also include lactose or milk sugar as well as high molecular weight polyethylene glycols. When aqueous suspensions and/or elixirs are desired for oral administration, the active ingredient may be combined with various sweetening or flavoring agents, coloring matter or dyes, and, if so desired, emulsifying and/or suspending agents as well, together with such diluents as water, ethanol, propylene glycol, glycerin and various like combinations thereof.

For parenteral administration (intramuscular, intraperitoneal, subcutaneous and intravenous use) a sterile injectable solution of the active ingredient is usually prepared. Solutions of a therapeutic compound of the present invention in either sesame or peanut oil or in aqueous propylene glycol may be employed. The aqueous solutions should be suitably adjusted and buffered, preferably at a pH of greater than 8, if necessary and the liquid diluent first rendered isotonic. These aqueous solutions are suitable intravenous injection purposes. The oily solutions are suitable for intraarticular, intramuscular and subcutaneous injection purposes. The preparation of all these solutions under sterile conditions is readily accomplished by standard pharmaceutical techniques well known to those skilled in the art.

For topical ocular administration, direct application to the affected eye may be employed in the form of a formulation as eyedrops, aerosol, gels or ointments, or can be incorporated into collagen (such as poly-2-hydroxyethylmethacrylate and co-polymers thereof), or a hydrophilic polymer shield. The materials can also be applied as a contact lens or via a local reservoir or as a subconjunctival formulation.

For intraorbital administration a sterile injectable solution of the active ingredient is usually prepared. Solutions of a therapeutic compound of the present invention in an aqueous solution or suspension (particle size less than 10 micron) may be employed. The aqueous solutions should be suitably adjusted and buffered, preferably at a pH between 5 and 8, if necessary and the liquid diluent first rendered isotonic. Small amounts of polymers can be added to increase viscosity or for sustained release (such as cellulosic polymers, Dextran, polyethylene glycol, or alginic acid). These solutions are suitable for intraorbital injection purposes. The preparation of all these solutions under sterile conditions is readily accomplished by standard pharmaceutical techniques well known to those skilled in the art. In the case of animals, compounds can be administered intraorbitally at dosage levels of about 0.1 to 50 mg/kg/day, advantageously 0.2 to 10 mg/kg/day given in a single dose or up to 3 divided doses.

The active compounds of the invention may also be formulated in rectal compositions such as suppositories or retention enemas, e.g., containing conventional suppository bases such as cocoa butter or other glycerides.

For intranasal administration or administration by inhalation, the active compounds of the invention are conveniently delivered in the form of a solution or suspension from a pump spray container that is squeezed or pumped by the patient or as an aerosol spray presentation from a pressurized container or a nebulizer, with the use of a suitable propellant, e.g., dichlorodifluoromethane, trichlorofluoromethane, dichlorotetrafluoroethane, carbon dioxide or other suitable gas. In the case of a pressurized aerosol, the dosage unit may be determined by providing a valve to deliver a metered amount. The pressurized container or nebulizer may contain a solution or suspension of the active compound. Capsules and cartridges (made, for example, from gelatin) for use in an inhaler or insufflator may be formulated containing a powder mix of a compound of the invention and a suitable powder base such as lactose or starch.

The following Examples illustrate the preparation of the compounds of the present invention. Melting points are uncorrected. NMR data are reported in parts per million ($\delta$) and are referenced to the deuterium lock signal from the sample solvent (deuteriodimethylsulfoxide unless otherwise specified). Commercial reagents were utilized without further purification. THF refers to tetrahydrofuran. DMF refers to N,N-dimethylformamide. Chromatography refers to column chromatography performed using 32–63 mm silica gel and executed upressure (flashpressure (flash chromatography) condition 25° C. All non-aqueous reactions were run under a nitrogen atmosphere for convenience and to maximize yields. Concentration at reduced pressure means that a rotary evaporator was used.

EXAMPLE 1

3-[[4-(4-FLUOROPHENOXY) PHENYLSULFONYL]-1-1](N-HYDROXYCARBAMOYL)-CYCLOBUTYLlAMINOlPROPIONIC ACID

A) Ethyl 1-azidocyclobutane-1-carboxvlate:

To a flask was added ethyl 1-bromocyclobutane-1-carboxylate (5.0 g, 25 mmol), dimethylformamide (120 mL), and sodium azide (2.43 g, 37.5 mmol). After stirring at room temperature for 2 days, the reaction was taken up in ether and washed with water (3×150 mL). The organic layer was removed and dried over magnesium sulfate. The drying reagent was removed by vacuum filtration and the solvent removed by rotary evaporator to give a colorless liquid, 3.69 g, yield 87%.

$^1$H-NMR (CDCl$_3$) $\delta$1.29 (t, 3H), 2.00 (m, 2H), 2.25 (m, 2H), 2.55 (m, 2H), 4.22 (q, 2H), IR (neat) 2109 cm-1.

B) Ethyl 1-aminocvclobutane-1-carboxylate hydrochloride:

Ethyl 1-azidocyclobutane-1-carboxylate (15.98 g, 94 mmol) was hydrogenated over 5% palladium over carbon (2 g) with concentrated hydrochloric acid (8 mL) in ethanol (250 mL) at 40 psi at room temperature. After about 3 hours, the catalyst was removed by vacuum filtration and the solvent removed by rotary evaporator yielding a white solid, 16.52 g, yield 97%.

$^1$H-NMR (CDCl$_3$) $\delta$1.34 (t, 3H), 2.15 (m, 1H), 2.30 (m, 1H), 2.70 (m, 2H), 2.80 (m, 1H), 4.30 (q, 2H), 9.05 (br s, 2H).

C) Benzvl 1-aminocyclobutane-1-carboxylate tosylate:

To a flask was added ethyl 1-aminocyclobutane-1-carboxylate hydrochloride (4.97 g, 29.6 mmol), p-toluene sulfonic acid (6.27 g, 33 mmol), benzyl alcohol (83 mL), and toluene (138 mL). The reaction was refluxed for 2 days with a Dean-Stark trap. After cooling to room temperature the solvent was removed by rotary evaporator. The residue was taken up in ether and placed in a freezer overnight. The resulting white solid was collected and dried, 5.27, g yield 93%.

$^1$H-NMR (CDCl$_3$) $\delta$1.90 (m , 2H), 2.30 (s, 3H), 2.40 (m, 2H), 2.55 (m, 2H), 5.10 (s, 2H), 7.05 (d, 2H), 7.25 (br s, 5H), 7.70 (d, 2H), 8.50 (br s, 2H); Atmospheric Pressure Chemical Ionization Mass Spectrum: 206 (M$^+$+1).

D) Benzyl 1-[4-(4-fluorophenoxyl)phenylsulfonylamino] cyclobutane-1- carboxylate:

Benzyl 1-aminocyclobutane-1-carboxylate tosylate (27.60 g, 70 mmol) was taken up in methylene chloride and washed with an excess of saturated sodium bicarbonate solution. The organic layer was dried over magnesium sulfate. The drying reagent was removed by vacuum filtration and the solvent removed by rotary evaporator. To the residue was added 4-(4-fluorophenoxy)phenylsulfonyl chloride (20.10 g, 70 mmol), triethyl amine (8.48 g, 11.6 mL, 84 mmol), and dimethylformamide (150 mL), and the reaction was stirred overnight at room temperature. The reaction was diluted with ether and washed with 1N hydrochloric acid (3×150 mL), water (2×200 mL), and saturated brine (1×150 mL). The organic layer was separated and dried over magnesium sulfate. The drying reagent was removed by vacuum filtration and the solvent removed by rotary evaporator to give a light brown solid, 24.45 g. A second crop was obtained by thoroughly washing the drying reagent with methylene chloride yielding after evaporation 4.2 g of a white solid, total yield 90%.

$^1$H-NMR (CDCl$_3$) $\delta$1.95 (m, 2H), 2.45 (m, 2H), 5.00 (s, 2H), 6.95 (m, 2H), 7.00 (m, 2H), 7.05 (m, 2H), 7.25 (br s, 3H), 7.30 (m, 2H), 7.35 (m, 2H), 7.75 (d, 2H); Atmospheric Pressure Chemical Ionization Mass Spectrum: 456 (M$^+$+1).

E) cis and trans Benzyl 1-{N-(2-ethoxvcarbonylethenyl)-N-[4-(4-fluorophenoxy)phenylsulfonyl]-amino}-cyclobutane-1 -carboxylate:

To a flask was added benzyl 1-[4-(4-fluorophenoxyl) phenylsulfonylamino]cyclobutane-1-carboxylate (10.0 g, 22 mmol), t-BuOH (75 mL), cesium carbonate (7.16 g, 22 mmol), and ethyl propiolate (4.31 g, 44 mmol, 4.45 mL, d=0.968). After stirring for about 1 hour the reaction turned dark red. After stirring 5 hours at room temperature the reaction was diluted with toluene and the cesium carbonate filtered off by vacuum filtration. The filtrate was washed with water and brine and dried over magnesium sulfate. The drying reagent was removed by vacuum filtration and the solvent removed by rotary evaporator to give a brick red oil. This was chromatographed (50 mm column; 15% EtOAc:85% hexane) to give a yellow oil, 5.12 g, yield 42%. A second portion was obtained by rechromatographing the mixed fractions yielding a yellow oil, 2.72 g, yield 22% (total yield 64%).

Atmospheric Pressure Chemical Ionization Mass Spectrum: 554 (M$^+$+1).

F) 1-{N-(2-Ethoxycarbonylethyl)-N-[4-(4-fluorophenoxy)phenvisulfonyl]-amino}cyclobutane-1-carboxylic acid:

A mixture of cis and trans benzyl 1-{N-(2-ethoxycarbonylethenyl)-N-[4-(4-fluorophenoxy)- phenylsulfonyl]amino}cyclobutane-1-carboxylate (11.57 g, 20.9 mmol) was hydrogenated over 10% palladium on carbon in ethanol (500 mL) for about 24 hours at room temperature at 40 psi. The catalyst was removed by vacuum filtration and the filtrate hydrogenated as above over 10% palladium on carbon (8 g) for about 2 days. The catalyst was removed by vacuum filtration and the solvent removed by rotary evaporator to give a thick yellow oil, 4.48 g, yield 46%.

$^1$H-NMR (CDCl) δ1.24 (t, 3H), 1.80 (m, 1H), 2.10 (m, 1H), 2.45 (m, 2H), 2.60 (m, 2H), 2.75 (m, 2H), 3.55 (m, 2H), 4.12 (q, 2H), 7.00 (d, 2H), 7.10 (m, 4H), 7.80 (d, 2H); Atmospheric Pressure Chemical Ionization Mass Spectrum: 456 (M$^+$+1); HPLC (C18 NovaPak, 30% to 90% acetonitrile/water gradient) 18.6 min.

G) Ethyl 3-{1-[(N-benzyloxycarbamoyl)cyclobutyl-]-[4-(4-fluorophenoxy)phenylsulfonyl]amino}propionate:

To a flask was added 1-{N-(2-ethoxycarbonylethyl)-N-[4-(4-fluorophenoxy)phenylsulfonyl]-amino}cyclobutane-1-carboxylic acid (4.48 g, 9.6 mmol), BOP (4.64 g, 10.5 mmol), diisopropylethylamine (1.37 g, 10.5 mmol=1.8 mL @ d=0.742), and DMF (50 mL). The reaction stirred at room temperature for about 3 hours. To this mixture was added diisopropylethylamine (2.49 g, 19.2 mmol, 3.35 mL) and 0-benzyl hydroxylamine . hydrochloride (1.98 g, 12.48 mmol). After stirring overnight at room temperature the reaction was taken up in ether and washed with 1N hydrochloric acid (3×150 mL), water (3×100 mL), and brine (1×200 mL). The organic layer was dried over magnesium sulfate, filtered and the filtrate concentrated. The residue was chromatographed (20% ethyl acetate:80% hexane) to give a thick colorless oil, 4.82 g, yield 88%.

$^1$H-NMR (CDCl$_3$) δ1.23 (t, 3H), 1.60 (m, 1H), 1.80 (m, 1H), 2.20 (m, 2H), 2.55 (m, 4H), 3.45 (m, 2H), 4.08 (q, 2H), 4.97 (s, 2H), 7.00 (d, 2H), 7.10 (m, 4H), 7.25 (m, 3H), 7.35 (m, 2H), 7.75 (d, 2H), 9.70 (br s, 1H); Atmospheric Pressure Chemical Ionization Mass Spectrum: 571 (M$^+$+1).

H) Ethyl 3-[[4-(4-fluorophenoxy)phenylsulfonyl]-1-[(N-hydroxycarbamoyl)cyclobutyl]amino]propionate:

The ethyl 3-{1-[(N-benzyloxycarbamoyl)cyclobutyl]-[4-(4-fluorophenoxy)phenylsulfonyl]-amino}propionate (4.8 g, 8.4 mmol) was hydrogenated over 5% palladium on barium sulfate (2.5 g) in ethanol/ethylacetate (1:4) (70 mL) at 40 psi at room temperature for about 2.5 hours. The catalyst was removed by vacuum filtration and the solvent removed by rotary evaporator to give a white foam, 3.64 g, yield 90%.

$^1$H-NMR (DMSO-d6) δ1.14 (t, 3H), 1.65 (m, 2H), 2.40 (m, 4H), 2.65 (m, 2H), 3.40 (m, 2H), 4.00 (q, 2H), 7.05 (d, 2H), 7.20 (m, 2H), 7.25 (m, 2H), 7.75 (d, 2H), 8.90 (br, s 1H), 10.70 (br s, 1H); Atmospheric Pressure Chemical Ionization Mass Spectrum: 481 (M$^+$+1).

I) 3-[[4-(4-Fluorophenoxy)phenylsulfonyl]-1[(N-hydroxycarbamoyl)cyclobutyl]amino]propionic acid:

To a flask was added ethyl 3-[[4-(4-fluorophenoxy)phenylsulfonyl]-1-[(N-hydroxycarbamoyl)-cyclobutyl]amino]propionate (3.64 g, 7.6 mmol), ethanol (50 mL), lithium hydroxide hydrate (1.59 g, 38 mmol). After stirring overnight at room temperature the solvent was removed by rotary evaporator. The residue was taken up in ethyl acetate and washed with water (2×200 mL) and 1N hydrocloric acid (2×200 mL). The organic layer was removed and dried over magnesium sulfate. The drying reagent was removed by vacuum filtration and the solvent removed by rotary evaporator to give a white solid, 3.37 g, yield 98%. This was recrystalized from hexane/ethyl acetate to give white crystals, 2.23 g, yield 65%, mp 168–169° C.

$^1$H-NMR (DMSO-d6) δ1.60 (m, 2H), 2.35 (m, 4H), 2.55 (m, 2H), 3.35 (m, 2H), 7.00 (d, 2H), 7.20 (m, 2H), 7.25 (m, 2H), 7.75 (d, 2H), 8.85 (s, 1H), 10.65 (s, 1H), 12.25 (s, 1H); Atmospheric Pressure Chemical Ionization Mass Spectrum: 453 (M$^+$+1); HPLC (C18 NovaPak, 30% to 90% acetonitrile/water gradient) 9.9 min; Anal calc'd: C., 53.09; H, 4.68; N, 6.19; Found: C, 53.40; H, 4.68; N, 6.20.

What is claimed is:

1. A compound of the formula

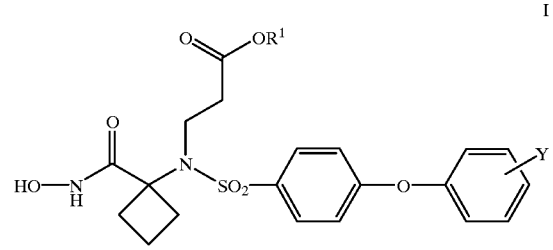

or the pharmaceutically acceptable salts thereof, wherein
R$^1$ is hydrogen or (C$_1$–C$_6$)alkyl; and
Y is selected from hydrogen, fluoro, chloro, trifluoromethyl, (C$_1$–C$_6$)alkoxy, trifluoromethoxy, difluoromethoxy and (C$_1$–C$_6$)alkyl.

2. A compound according to claim 1, wherein Y is hydrogen, fluoro or chloro.

3. A compound according to claim 1, wherein Y is 4-fluoro or 4-chloro.

4. A compound according to claim 1, wherein R$^1$ is hydrogen.

5. A compound according to claim 3, wherein R$^1$ is hydrogen.

6. A compound according to claim 1, wherein said compound is selected from the group consisting of:
3-[[4-(4-fluorophenoxy)benzenesulfonyl]-(1-hydroxycarbamoylcyclobutyl)amino]propionic acid ethyl ester, and
3-[[4-(4-fluorophenoxy)benzenesulfonyl]-(1-hydroxycarbamoylcyclobutyl) amino]propionic acid.

7. A pharmaceutical composition for the treatment of a condition selected from arthritis, inflammatory bowel disease, Crohn's disease, emphysema, chronic obstructive pulmonary disease, Alzheimer's disease, organ transplant toxicity, cachexia, allergic reactions, allergic contact hypersensitivity, cancer, tissue ulceration, restenosis, periodontal disease, epidermolysis bullosa, osteoporosis, loosening of artificial joint implants, atherosclerosis, aortic aneurysm, congestive heart failure, myocardial infarction, stroke, cerebral ischemia, head trauma, spinal chord injury, neuro-degenerative disorders, autoimmune disorders, Huntington's disease, Parkinson's disease, migraine, depression, peripheral neuropathy pain, cerebral amyloid angiopathy, nootropic or cognitive enhancement, amyotrophic lateral sclerosis, multiple sclerosis, ocular angiogenesis, corneal injury, mascular degeneration, abnormal wound healing, bums, diabetes, tumor invasion, tumor growth, tumor metastasis, comeal scarring, scleritis, AIDS, sepsis and septic shock in a mammal, comprising an amount of a compound of claim 1 or a pharmaceutically acceptable salt thereof, effective in such treatment and a pharmaceutically acceptable carrier.

8. A method for treating a condition selected from arthritis, inflammatory bowel disease, Crohn's disease, emphysema, chronic obstructive pulmonary disease, Alzheimer's disease, organ transplant toxicity, cachexia, allergic reactions, allergic contact hypersensitivity, cancer, tissue ulceration, restenosis, periodontal disease, epidermolysis bullosa, osteoporosis, loosening of artificial joint implants, atherosclerosis, aortic aneurysm, congestive heart failure, myocardial infarction, stroke, cerebral ischemia, head trauma, spinal chord injury, neuro-degenerative disorders, autoimmune disorders, Huntington's disease, Parkinson's disease, migraine, depression, peripheral neuropathy pain, cerebral amyloid angiopathy, nootropic or cognitive enhancement, amyotrophic lateral sclerosis, multiple sclerosis, ocular angiogenesis, corneal injury, mascular degeneration, abnormal wound healing, bums, diabetes, tumor invasion, tumor growth, tumor metastasis, corneal scarring, scleritis, AIDS, sepsis and septic shock in a mammal, comprising administering to said mammal an amount of a compound of claim 1 or a pharmaceutically acceptable salt thereof, effective in treating such a condition.

9. A pharmaceutical composition for the treatment of a condition which can be treated by the inhibition of matrix metalloproteinases in a mammal, comprising an amount of a compound of claim 1 effective in such treatment and a pharmaceutically acceptable carrier.

10. A pharmaceutical composition for the treatment of a condition which can be treated by the inhibition of a mammalian reprolysin in a mammal, comprising an amount of a compound of claim 1 effective in such treatment and a pharmaceutically acceptable carrier.

11. A method for the inhibition of matrix metalloproteinases in a mammal, comprising administering to said mammal an effective amount of a compound of claim 1.

12. A method for the inhibition of a mammalian reprolysin in a mammal, comprising administering to said mammal an effective amount of a compound of claim 1.

13. A pharmaceutical composition for selectively inhibiting matrix metalloproteinase-13, in a mammal comprising an effective amount of a compound of claim 1, or a pharmaceutically acceptable salt thereof, and a pharamaceutically acceptable carrier.

14. A method for the selective inhibition of matrix metalloproteinases-13 in a mammal comprising administering to said mammal an effective amount of a compound of claim 1 or a pharmaceutically acceptable salt thereof.

15. A method for treating arthritis in a mammal comprising administering to said mammal an amount of a compound of claim 1 or a pharmaceutically acceptable salt thereof, effective in treating such a condition.

* * * * *